United States Patent [19]

Sung

[11] Patent Number: 5,117,481
[45] Date of Patent: May 26, 1992

[54] DETACHABLE BATHING UNIT FOR FAR INFRARED BATH

[76] Inventor: Lai M. Sung, 8F, No. 1-3, Sec. 5, Chung Hsiao E. Rd., Taipei, Taiwan

[21] Appl. No.: 737,652

[22] Filed: Jul. 30, 1991

[51] Int. Cl.⁵ .................. A61H 33/06; F26B 19/00; F24C 1/14

[52] U.S. Cl. ................... 392/416; 392/375; 4/526; 52/585

[58] Field of Search ............ 392/416, 342, 360, 375; 4/526–532; 128/367, 368; 52/585

[56] References Cited

U.S. PATENT DOCUMENTS

| | | | |
|---|---|---|---|
| 1,582,766 | 4/1926 | Long | 4/527 |
| 2,346,827 | 4/1944 | Cotter | 4/527 |
| 2,539,710 | 1/1951 | Sziklay | 4/527 |
| 3,422,465 | 1/1969 | Jones et al. | 4/532 |
| 3,945,058 | 3/1976 | Gardner | 4/527 |

Primary Examiner—Bruce A. Reynolds
Assistant Examiner—John A. Jeffery
Attorney, Agent, or Firm—Bacon & Thomas

[57] ABSTRACT

A detachable bathing unit for far infrared bath, comprised of a base panel at the bottom, a first front panel and a second front panel bilaterally disposed at the front, a door panel disposed at the front between the first and second front panels, a first side panel disposed at one side, a second side panel disposed at an opposite side, a first back panel and a second back panels disposed at the back, a top panel disposed at the top and an electric control box mounted on the top panel at the top. The base, front, side, back and top panels are respectively connected into shape by means of tongue-and-groove joint and tenon-and-mortise joint so that they can be conveniently detached when not in use.

1 Claim, 4 Drawing Sheets

DETACHABLE BATHING UNIT FOR FAR INFRARED BATH

BACKGROUND OF THE INVENTION

The present invention relates to bathing units and relates more particularly to a detachable bathing unit for far infrared bath which can be detached to reduce space occupation when it is not in use and, which can be conveniently built up indoors as well as outdoors.

Various movable types of sauna bathing units have been known. Disadvantage of the conventional movable types of sauna bathing units is its fixed structure which is not detachable or collapsible, and therefore, much space shall be provided for storing a sauna bathing unit even when it is not in use.

The present invention has been accomplished to eliminate the aforesaid problem. It is therefore the main object of the present invention to provide a movable bathing unit which can be conveniently detached to reduce space occupation when it is not in use and, which can be conveniently built up indoors as well as outdoors.

DETAILED DESCRIPTION OF THE PREFERRED EMBODIMENT

Figure 1:
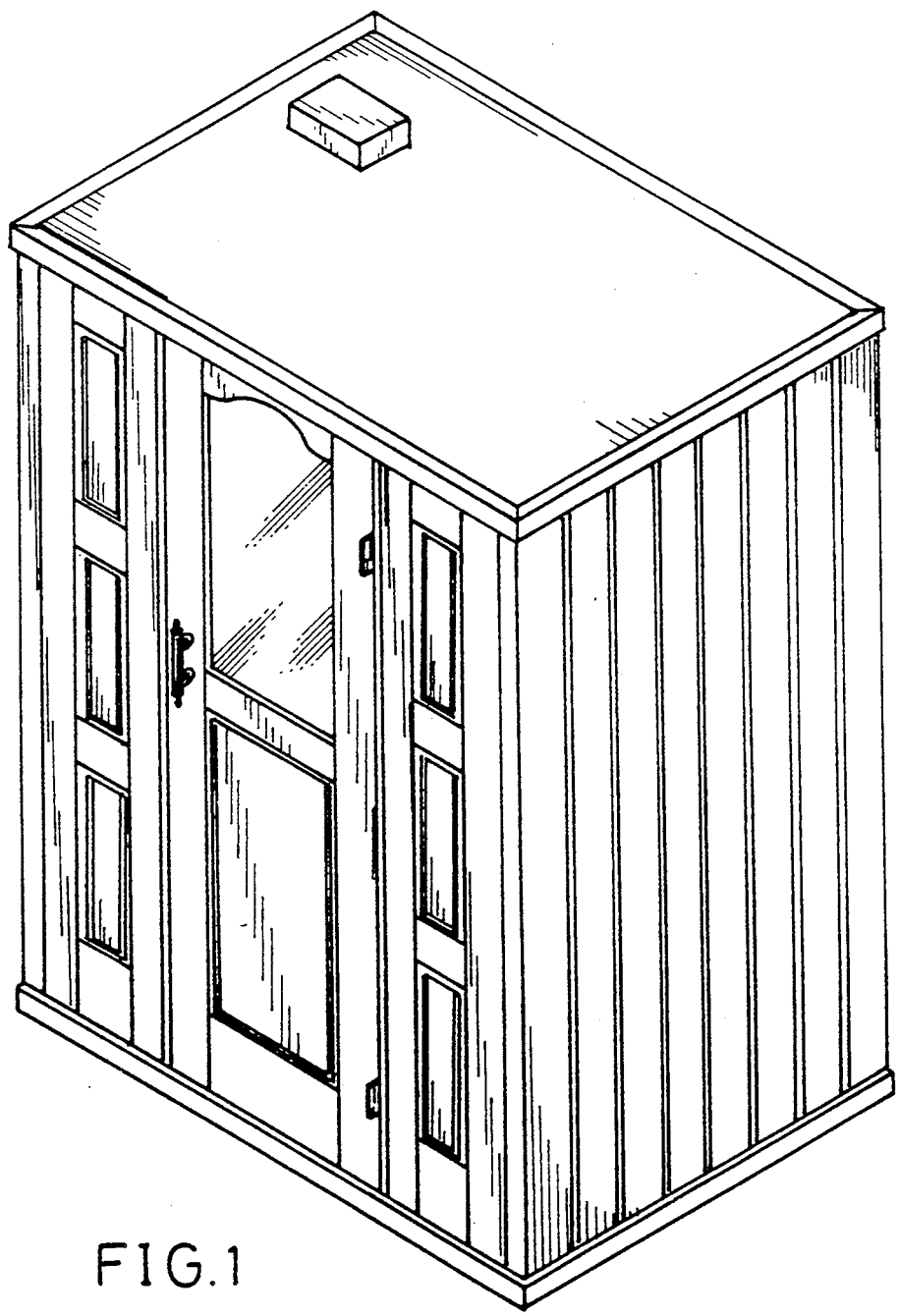
FIG. 1 is a perspective view of the preferred embodiment of the bath unit constructed according to the present invention.
Figure 2:
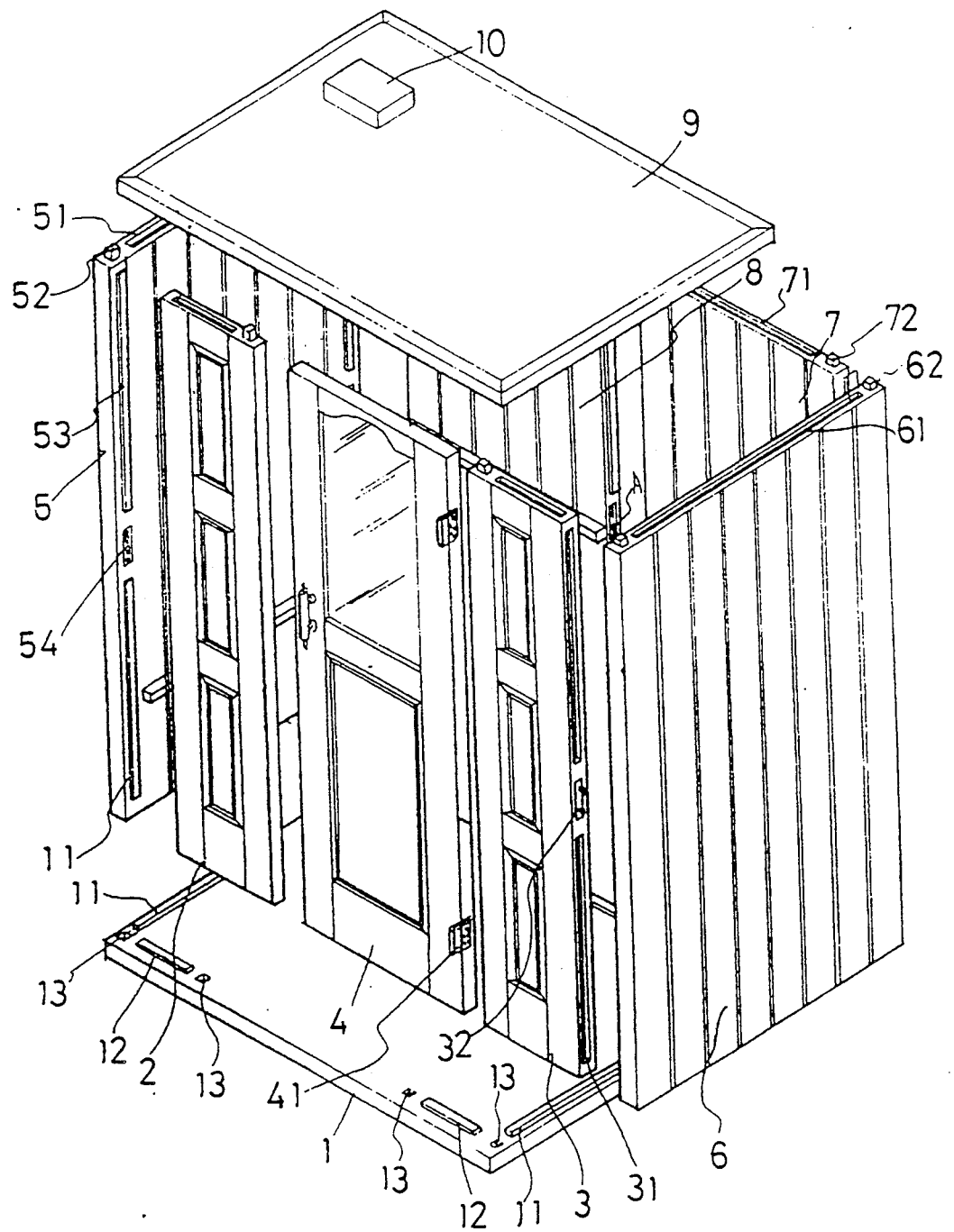
FIG. 2 is a dismantled perspective view thereof.

Referring to the annexed drawings in detail, a bathing unit as constructed in accordance with the present invention is made in a rectangular shape and comprised of a base panel 1 at the bottom, a first front panel 2 and a second front panel 3 bilaterally disposed at the front, a door panel 4 disposed at the front between the first and second front panels 2 and 3, a first side panel 5 disposed at one side, a second side panel 6 disposed at an opposite side, a first back panel 7 and a second back panels 8 disposed at the back, a top panel 9 disposed at the top and an electric control box 10 mounted on the top panel at the top.

The base panel 1 is made from a rectangular plate having on the top surface thereof a first pair of elongated projecting strips 11 transversely disposed at two opposite ends, a second pair of elongated projecting strips 12 longitudinally disposed at two opposite ends at one side, a third pair of elongated projecting strips (not shown) longitudinally disposed at two opposite ends at an opposite side, and a plurality of mortises 13 disposed at two opposite ends by each of the second and third pairs of elongated projecting strips respectively. The first and second front panels 2 and 3 are symmetrical in structure, each of which having two elongated grooves 21 or 31 longitudinally aligned on the peripheral edge thereof at one side with a connector 22 or 32 set therebetween, an elongated groove 23 or 33 and a tenon 24 or 34 on the top edge thereof, an elongated groove and a tenon on the bottom edge thereof (not shown). The first and second side panels 5 and 6 are symmetrical in structure, each of which having an elongated end groove 51 or 61 and two tenons 52 or 62 on the top edge as well as the bottom edge thereof (the tenons 52 or 62 are disposed at two opposite ends with the elongated end groove 51 or 62 disposed therebetween), a first pair of elongated side projecting strip 53 or 63 longitudinally aligned on the inner wall surface thereof at one side with a first connector 54 or 64 set therebetween, and a second pair of elongated side projecting strips 55 or 65 (not shown) longitudinally aligned on the inner wall surface thereof at an opposite side with a second connector 56 or 66 (not shown) set therebetween. The two back panels 7 and 8 are symmetrical in structure each of which having an elongated end groove 71 or 81 and two tenons 72 or 82 on the top edge as well as the bottom edge thereof, a first pair of elongated side grooves (not shown) longitudinally aligned on the peripheral edge thereof at one side with a first connector (not shown) set therebetween, and a second pair of elongated side grooves (not shown) longitudinally aligned on the peripheral edge thereof at an opposite side with a second connector (not shown) set therebetween. The top panel 9 has a plurality of projecting strips and mortises on the bottom surface around the periphery thereof corresponding to the elongated end grooves and tenons on the front, side and back panels.

The aforesaid parts can be conveniently built up into a bathing unit. The two front panels 2 and 3 are vertically fastened in the base panel 1 at the front by inserting the elongated end grooves 23 and 33 and the tenons 24 and 34 on the bottom edge of the front panels 2 and 3 in the second pair of elongated projecting strips 12 and the corresponding mortises on the base panel 1. Then, the door 4 set above the base panel 1 between the first and second front panels 2 and 3 and hinged to the second front panel 3 by hinges 41. Then, the first and second side panels 5 and 6 are respectively mounted on the base panel 1 at the top and connected to the first and second front panels 2 and 3 by fastening the elongated end grooves 51 and 61 and the tenons 52 and 62 on the bottom edge of the first and second side panels 5 and 6 in the first pair of elongated projecting strips 11 and the corresponding mortises 13 on the base panel 1 and by fastening the first pair of elongated side projecting strips 53 and 63 and the first connectors 54 and 64 of the first and second side panels 5 and 6 in the elongated grooves 21 and 31 and the connector 22 and 32 of the first and second front panels 2 and 3. Then, the back panels 7 and 8 are vertically fastened in the base panel 1 at the back and respectively connected to the first and second side panels 5 and 6 by fastening the elongated end grooves 71 and 81 and the tenons 72 and 82 on the bottom edge of the first and second back panels 7 and 8 in the third pair of elongated projecting strips and the corresponding mortises on the base panel 1 and by fastening the first pair of elongated side grooves and the first connector of each back panel 7 or 8 in the second pair of elongated side projecting strips 55 or 65 and the second connector 56 or 66 of the first or second side panel 5 or 6. Then, the top panel 9 is attached to the front, side and back panels 2, 3, 4, 5, 6, 7 and 8 at the top with the elongated projecting strips and mortises thereof respectively fastened in the corresponding elongated grooves and tenons on the front, side and back panels 2, 3, 4, 5, 6, 7 and 8.

Figure 3:
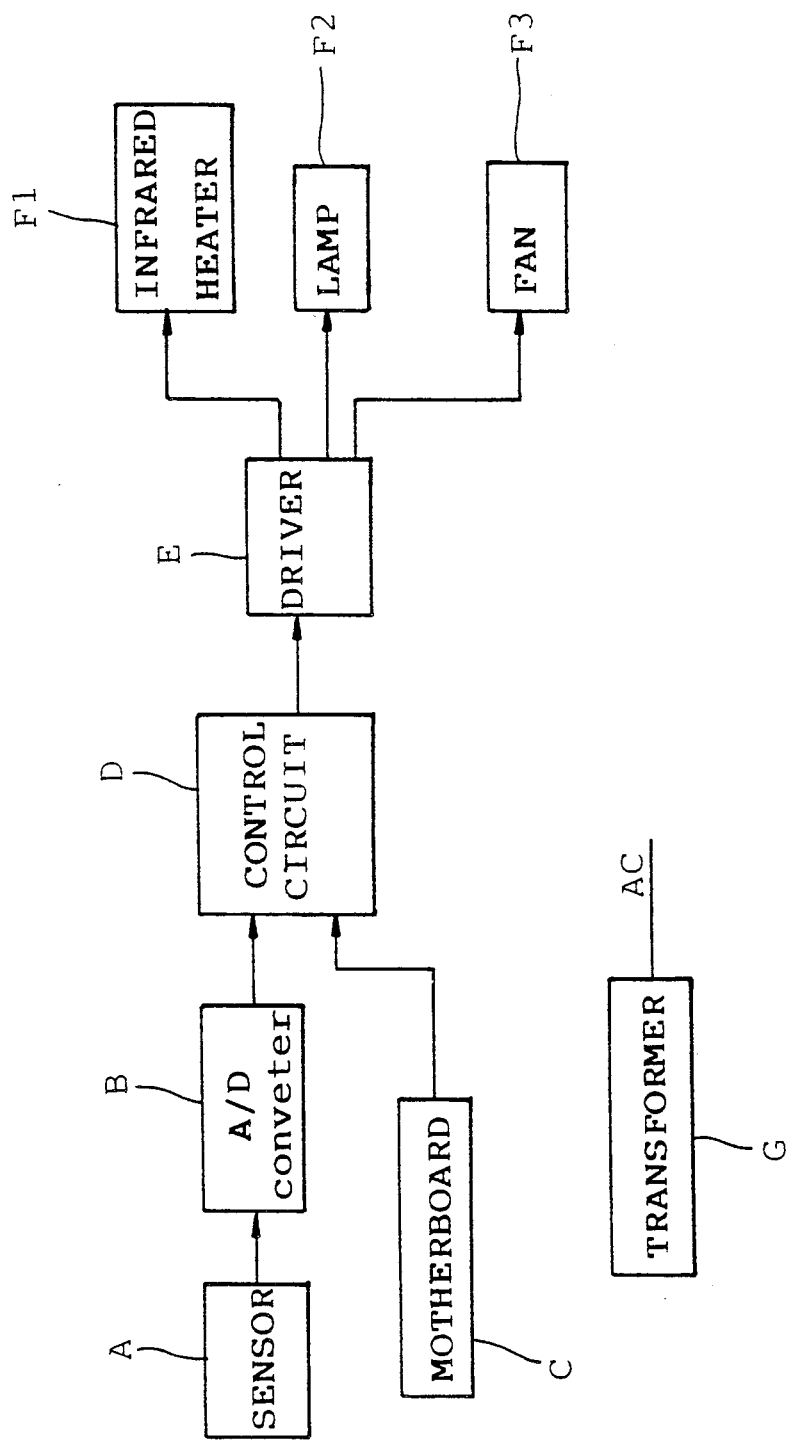
FIGS. 3 and 4 illustrate the internal arrangement of the electric control box.
Figure 4:
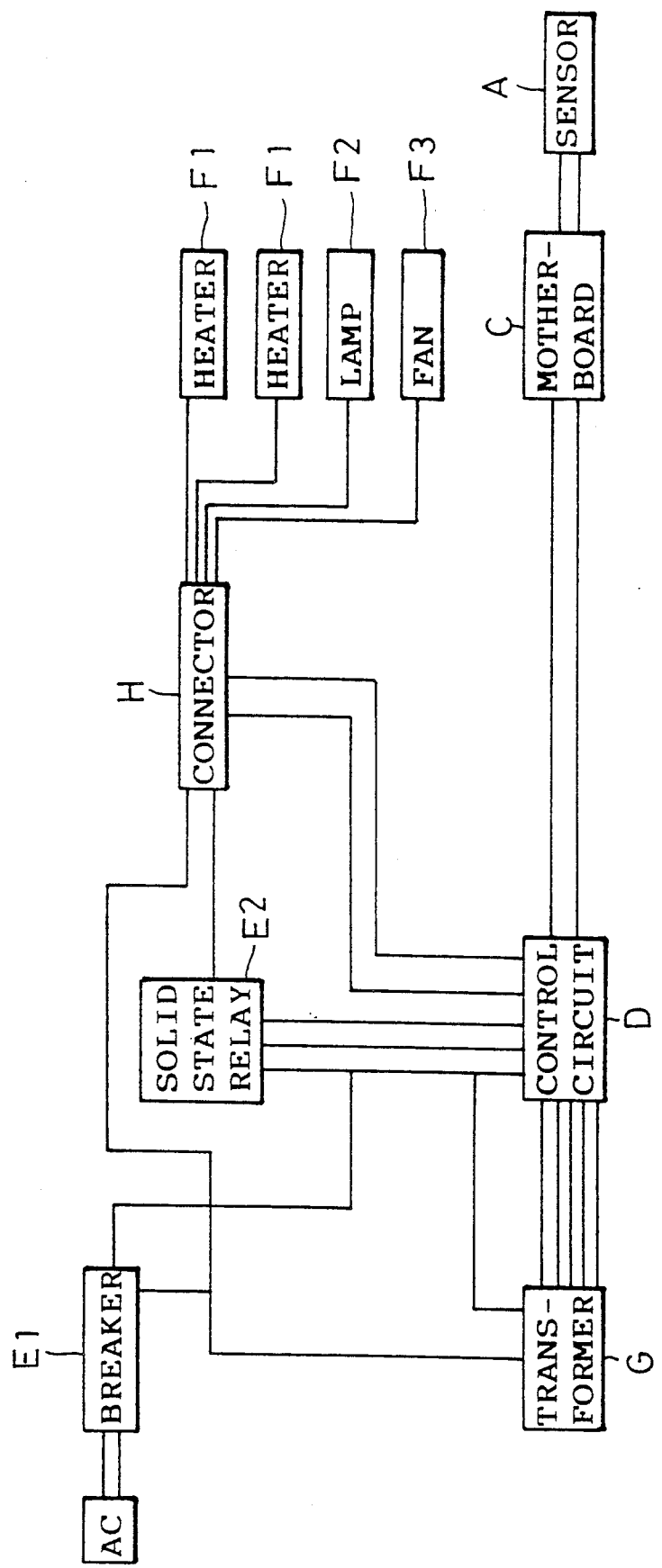

Referring to FIG. 3, the electric control box 10 is a requisite electric apparatus in a regular sauna bath unit which comprises a temperature sensor A to provide a signal to an analog/digital converter B and a motherboard C which comprises a time display and a keyboard input circuit. Signals from the converter B and the motherboard C are sent to a microprocessing unit to trigger a control circuit D which provides signals to turned on/off an infrared heater F1, an electric lamp F2 and an electric fan F3. Referring to FIG. 4, the power transformer G provides all necessary working voltage. When the motherboard B receives a signal from the temperature sensor A, it sends out a predetermined temperature and time data to the power supply and the control board so as to further causes the control circuit E, which is consisted of a breaker E1 and a solid state relay E2, to send corresponding signals to the three loads F1, F2 and F3 via a connector H. Therefore, the electric control box 10 can be set to produce heat according to individual preference. Once the temperature inside the bathing unit exceeds the desired range, a short warning sound will be produced twice. When predetermined length of time is up, a long warning sound will be produced and, the power supply will be automatically cut off thereafter to stop the operation.

What is claimed is:

1. A bathing unit for far infrared bath, comprising:

a base panel transversely disposed at the bottom, said base panel having on the top surface thereof a first pair of elongated projecting strips transversely disposed at two opposite ends, a second pair of elongated projecting strips longitudinally disposed at two opposite ends at one side, a third pair of elongated projecting strips longitudinally disposed at two opposite ends at an opposite side, and a plurality of mortises disposed at two opposite ends by each of the second and third pairs of elongated projecting strips respectively;

a first front panel and a second front panel vertically fastened in said base panel at the front, said first and second front panel each having two elongated grooves longitudinally aligned on the peripheral edge thereof at one side with a connector set therebetween, an elongated groove and a tenon on the top edge thereof, an elongated groove and a tenon on the bottom edge thereof;

a door panel set between said first and second front panel and pivoted to said second front panel;

a first side panel and second side panel vertically fastened in said base panel at two opposite sides, said first and second side panels each having an elongated end groove and two tenons each on the top edge and the bottom edge thereof, a first pair of elongated side projecting strip longitudinally aligned on the inner wall surface thereof at one side with a first connector set therebetween, and a second pair of elongated side projecting strips longitudinally aligned on the inner wall surface thereof at an opposite side with a second connector set therebetween;

two back panels vertically fastened in said base panel at the back and respectively connected to said first and second side panels, said two back panels each having an elongated end groove and two tenons each on the top edge and the bottom edge thereof, a first pair of elongated side grooves longitudinally aligned on the peripheral edge thereof at one side with a first connector set therebetween, and a second pair of elongated side grooves longitudinally aligned on the peripheral edge thereof at an opposite side with a second connector set therebetween;

a top panel mounted on said first and second front panels, said first and second side panels and said two back panels at the top, said top panel having a plurality of projecting strips and mortises on the bottom surface around the periphery thereof; and wherein:

said first and second front panels are vertically fastened in said base panel at the front by inserting the elongated end grooves and the tenons on the bottom edges of the front panels in the second pair of elongated projecting strips and the corresponding mortises on said base panel; said first and second side panels are respectively mounted on said base panel at the top and connected to said first and second front panels by fastening the elongated end grooves and the tenons on the bottom edge of said first and second side panels in the first pair of elongated projecting strips and the corresponding mortises on said base panel and by fastening the first pair of elongated side projecting strips and the first connectors of said first and second side panels in the elongated grooves and the connector of said first and second front panels; said back panels are vertically fastened in said base panel at the back and respectively connected to said first and second side panels by fastening the elongated end grooves and the tenons on the bottom edge of said first and second back panels in the third pair of elongated projecting strips and the corresponding mortises on said base panel and by fastening the first pair of elongated side grooves and the first connector of each back panel in the second pair of elongated side projecting strips and the second connector of said first or second side panel; said top panel is attached to said front, side and back panels at the top with the elongated projecting strips and mortises thereof respectively fastened in the corresponding elongated grooves and tenons on the front, side and back panels.

* * * * *